(12) United States Patent
Lopez et al.

(10) Patent No.: US 8,343,917 B2
(45) Date of Patent: Jan. 1, 2013

(54) COMBINATION OF ERYTHROPOIETIN GLYCOISOFORMS

(75) Inventors: Ricardo Agustin Lopez, Santa Fe (AR); Marcelo Gustavo Daelli, Santa Fe (AR); Dardo Alexis Pereira Bacci, Santa Fe (AR); Gabriel Ignacio Amadeo, Santa Fe (AR); Miriam Patricia Pereiro, Santa Fe (AR); Cristina Noemi Artana, Santa Fe (AR); Nestor Maskin, Santa Fe (AR); Bernardo Cesar Pistillo, Santa Fe (AR); Carolina Didier, Santa Fe (AR); Marina Etcheverrigaray, Santa Fe (AR); Ricardo Kratje, Santa Fe (AR)

(73) Assignee: Protech Pharma, SA, Santa Fe (AR)

( * ) Notice: Subject to any disclaimer, the term of this patent is extended or adjusted under 35 U.S.C. 154(b) by 729 days.

(21) Appl. No.: 12/093,365

(22) PCT Filed: Nov. 7, 2006

(86) PCT No.: PCT/ES2006/070171
§ 371 (c)(1),
(2), (4) Date: Nov. 25, 2008

(87) PCT Pub. No.: WO2007/054600
PCT Pub. Date: May 18, 2007

(65) Prior Publication Data
US 2009/0220595 A1    Sep. 3, 2009

(30) Foreign Application Priority Data

Nov. 10, 2005 (AR) .................... P050104712

(51) Int. Cl.
*A61K 38/18* (2006.01)
*A61K 9/20* (2006.01)
*A61K 9/46* (2006.01)
*C07K 14/505* (2006.01)
*C12N 5/00* (2006.01)
*C12N 15/09* (2006.01)

(52) U.S. Cl. ........ 514/7.7; 530/397; 435/69.1; 435/325; 424/464; 424/466

(58) Field of Classification Search .................. None
See application file for complete search history.

(56) References Cited

U.S. PATENT DOCUMENTS

| | | | |
|---|---|---|---|
| 5,856,298 A | 1/1999 | Strickland | |
| 6,165,783 A | 12/2000 | Weiss et al. | |
| 6,268,336 B1 | 7/2001 | Nitsu et al. | |
| 6,531,121 B2 | 3/2003 | Brines et al. | |
| 6,673,575 B1 | 1/2004 | Franze et al. | |
| 6,784,154 B2 | 8/2004 | Westenfelder | |
| 7,012,130 B1 * | 3/2006 | Carcagno et al. ............. | 530/350 |
| 2002/0169129 A1 | 11/2002 | Zaharia | |
| 2004/0018978 A1 | 1/2004 | Campana et al. | |
| 2004/0198663 A1 | 10/2004 | Baker et al. | |
| 2005/0181359 A1 | 8/2005 | Optelten et al. | |

FOREIGN PATENT DOCUMENTS

| | | |
|---|---|---|
| EP | 0 411 678 A1 | 2/1991 |
| WO | WO 00/63403 | 10/2000 |
| WO | WO 03/046162 A2 | 6/2003 |
| WO | WO 03/046187 A1 | 6/2003 |
| WO | WO 03/057242 A1 | 7/2003 |
| WO | WO 2004/012759 A2 | 2/2004 |

OTHER PUBLICATIONS

Mitra et al. N-linked oligosaccharides as outfitters for glycoprotein folding, form and function. TRENDS in Biochemical Sciences. vol. 31, No. 3, (Mar. 2006).*
Schlags et al. Two-dimensional electrophoresis of recombinant human erythropoietin: A future method for the European Pharmacopoeia? Proteomics 2:679-682 (2002).*

* cited by examiner

*Primary Examiner* — Elizabeth C Kemmerer
*Assistant Examiner* — Regina M Deberry
(74) *Attorney, Agent, or Firm* — RatnerPrestia

(57) ABSTRACT

This invention relates to a combination of erythropoietin glycoisoforms, wherein such glycoisoforms may include a quantity of sialic acid ranging from 4 to 10 molecules of sialic acid per molecule of erythropoietin. The combination of glycoisoforms can be used for the treatment or prevention of sepsis, and used to prepare a pharmaceutical composition including such combination. The invention also encompasses a cell line producing a combination of erythropoietin glycoisoforms, procedures to obtain the cell line, a procedure to produce such a combination of glycoisoforms, and methods of treatment and prevention of sepsis.

6 Claims, 11 Drawing Sheets
(5 of 11 Drawing Sheet(s) Filed in Color)

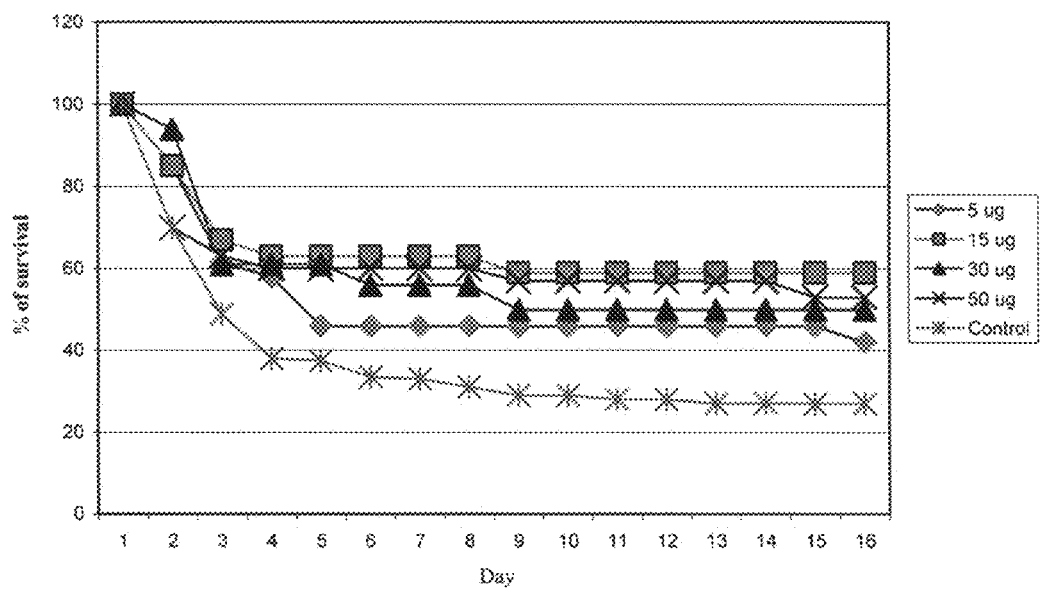
Figure: 4

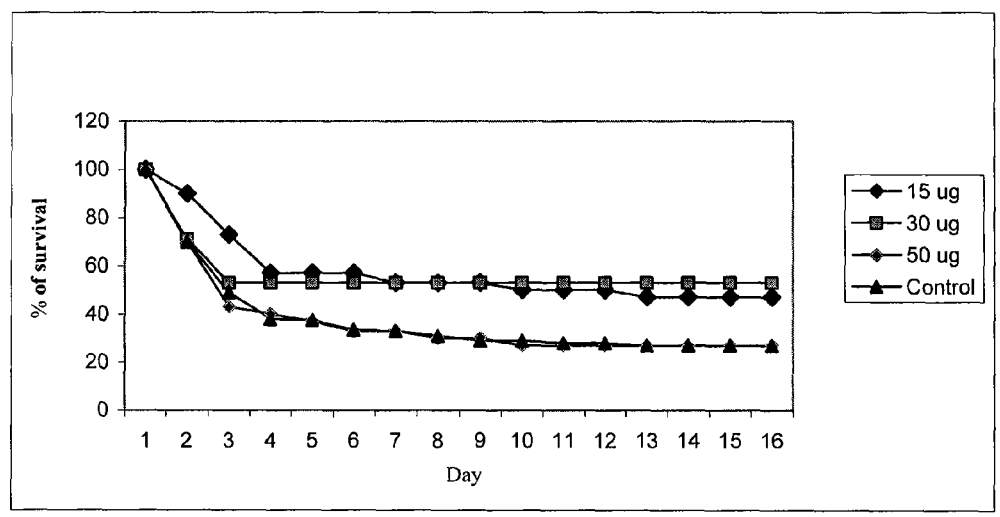
Figure: 5

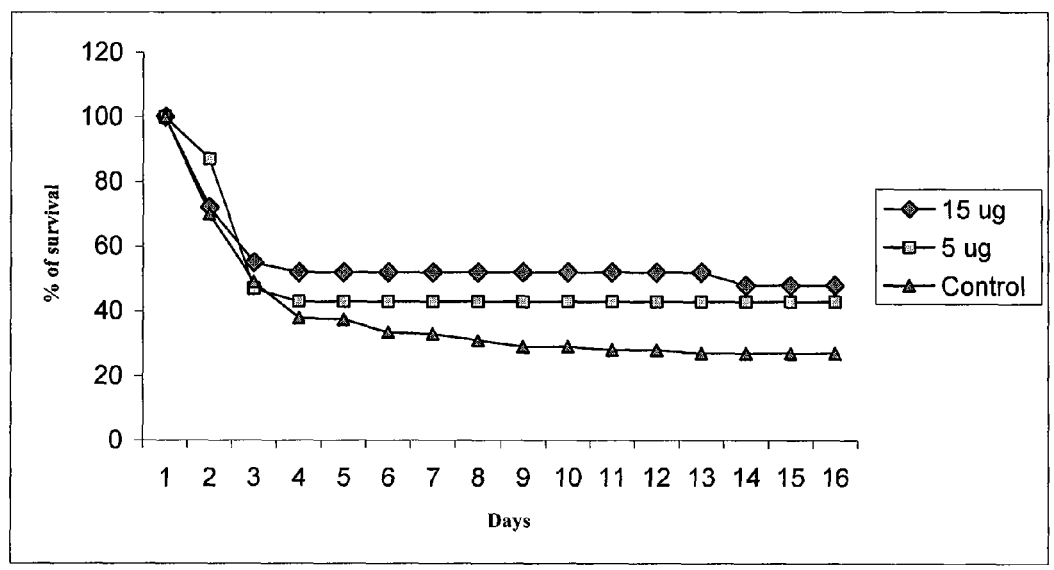
Figure: 6

COMBINATION OF ERYTHROPOIETIN GLYCOISOFORMS

This application is a U.S. National Phase application of PCT Application No. PCT/ES2006/070171, filed Nov. 10, 2005.

FIELD OF THE INVENTION

This invention refers to a transgenic cell line that produces a combination of erythropoietin glycoisoforms, wherein such glycoisoforms can comprise a quantity of sialic acid ranging from 4 to 10 molecules of sialic acid per erythropoietin molecule, the combination of glycoisoforms for the treatment or prevention of sepsis, a pharmaceutical composition comprising such combination, procedures to obtain the cell line, procedure to produce such combination of glycoisoforms, and sepsis treatment and prevention methods.

BACKGROUND OF THE INVENTION

The modifications produced by eukaryotic cells on the glycoprotein glycosialation pattern may affect some of their biological properties such as their transport, secretion, stability and interaction with other molecules and receptors (Witter, A. and Howard, S., Biochem. 29: 4175-4180, 1990; Hart, Curr. Op. Cell Biol. 4: 1017-1023, 1992; Gooche et al., Bio/Technology 9: 1347-1355, 1991; Parekh et al., Curr. Op. Cell. Biol. 1: 750-754, 1991; Bevilacqua, M. and Nelson, R., J. Clin. Invest. 91: 379-387, 1993; Nelson et al., J. Clin. Invest. 91: 1157-1166, 1993; Norgard, et al., Proc. Natl. Acad. Sci. USA 90: 1068-1072, 1993; Imai et al., Nature 361: 555-557, 1993).

Human erythropoietin (EPO), a protein broadly used for erythropoiesis stimulation, in its natural and recombinant (produced in transgenic eukaryotic cell lines) forms contains four complex oligosaccharide chains attached to the polypeptide chain. Three of the attachments are N-type and one is O-type. Its specific location is well known (Elliott, S. et al. The Journal of Biological Chemistry 279(16): 16854-16862, 2004; Watson et al., Glycobiology 4(2): 227-237, 1994). Oligosaccharides with N-type attachments may contain a variable number of terminal residues of sialic acid, a fact that remarkably affects EPO activity (Egrie, J. and Browne, J., Br. J. Cancer 84(1): 3-10, 2001; Goldwasser et al., J. Biol. Chem. 249: 4202-4206, 1974). For instance, a higher quantity of sialic acid extends the EPO half-life in blood, but reduces affinity to the receptor related to its hematopoietic activity. Conversely, an EPO with lower or non-existent content of sialic acid has a low in vivo half-life and a high affinity level to its receptor related to its hematopoietic activity (Fukuda et al., Blood 73: 84-89, 1989; Spivak, J. and Hogans, B., Blood 73: 90-99, 1989; Imai et al., Eur. J. Biochem. 194: 457-462, 1990; Higuchi et al., J. Biol. Chem. 267(11): 7703-7709, 1991). In order to act as an in vivo erythropoiesis stimulant, EPO must be continuously present in the blood in adequate concentrations and, therefore, a long in vivo life term remarkably enhances its erythropoietic action. In contrast, when present in vivo in high concentrations for short periods it has a protective effect on tissues (Morishita, E. et al.; Neuroscience 76: 105-116, 1997), a fact that suggests that EPO with low or non-existent levels of sialic acid is useful for the induction of tissue protection with no consequential erythropoietic effects. This would be very significant, since red blood cell increase in blood may be highly risky. On the other hand, if the EPO does not contain sialic acid (asialo-EPO), its in vivo half-life is excessively short and, therefore, it is not useful either for erythropoiesis stimulation or tissue protection.

It is known that the recombinant EPO produced in eukaryotic cell lines is a combination of molecular species that share the same polypeptide chain but have different quantities of terminal sialic acid present in the oligosaccharidic chains. These diverse forms of EPO are known as EPO glycoisoforms. As these EPO glycoisoforms have different charges, each can be isolated from the rest by means of, for instance, the isoelectrofocusing technique. The mixture of EPO glycoisoforms produced by recombinant cells may vary according to the cell line in use. For example, when the EPO is produced in CHO cells the glycoisoforms contain from 1 to 14 molecules of sialic acid.

Beyond EPO practical use in erythropoiesis stimulation, and mainly due to its protective effect on tissue, EPO has been proposed as an active principle in the treatment of diverse anomalies and diseases. For instance, the patent application by Baker et al., U.S. Pub. Applic. No. 2004/0198663, describes a method for reducing the effects of myocardial ischemia and its associated damage by the administration of effective quantities of erythropoietin. The patent document by Weiss, S. et al., U.S. Pat. No. 6,165,783, describes a method to induce the differentiation of neural stem cells or treat neurodegenerative diseases through the application of effective quantities of erythropoietin. The patent application by Zaharia, V., U.S. Pub. Applic. No. 2002/0169129, describes a method comprising the administration of an effective dose of human recombinant EPO to improve life quality of a patient. The patent application by Campana W. M. et al., U.S. Pub. Applic. No. 2004/0018978, describes a method for neuropathic pain treatment and for the protection of the peripheral nervous system that comprises the administration of erythropoietin. U.S. Pat. No. 6,268,336 describes a method for treating hepatic diseases that comprises the administration of erythropoietin. Patent document WO 03/057242 by Van Gilst, W. H. et al., describes the use of erythropoietin for the treatment or prevention of cardiac deficiencies. U.S. Pat. No. 6,784,154 by Westenfelder, Ch. describes a method for renal protection and for the treatment of acute ischemic renal failure that comprises the administration of erythropoietin. Patent document WO 04/012759 by Haller H. et al. describes the use of erythropoietin for stimulation, mobilization, proliferation and differentiation of endothelial stem cells.

For many years, researchers focused on obtaining erythropoietins with high sialic acid levels in order to ensure a high plasma half-life, increasing, for instance, glycosialation sites or enriching the erythropoietin glycoisoforms with high sialic acid levels (see U.S. Pat. No. 5,856,298 by Strickland, T. W.). Another procedure to increase glycosialation is described in U.S. Pat. No. 6,673,575 by Franze R. et al.; and patent document WO 03/080852 describes a chromatographic process to produce high-purity erythropoietin with a desired glycoisoform profile.

On the other hand, U.S. Pat. No. 6,531,121 by Bines, M. et al. describes the administration of asialo-erythropoietin for the protection and maintenance of cell, tissue or organ viability, proving that asialo-erythropoietin (asialo-EPO) activity is different from that of the previously described ones.

Sepsis is the systemic response to infection. This response may occasionally be exacerbated and affect the functions of organs such as kidneys, liver, heart, lungs, intestines, pancreas, CNS, adrenals, and bone marrow. It may also alter metabolism, coagulation, immunological system, regional perfusion of organs and systemic circulation, causing a septic shock. Septic mortality increases at a rate directly proportional to the shock presence and seriousness, and to the number of organ failures, ranging from 30% if no failure is involved to 100% in cases where failures occur in four or more organs (Fry, D. E., Pearlstein, L., Fulton, R. L. et al., Multiple System Organ Failure. The Role of Uncontrolled Infection, Arch. Surg. 115: 136-140, 1980). Despite the developments achieved so far, sepsis remains the main cause of mortality in non-coronary intensive care units (Angus, D. C. et al., Crit. Care Med. 29: 1303-10, 2001). Current therapeutic bases are: plasma volume expansion using crystalloids and/or colloids; support to failing organs, including those in shock; glycemia strict control; use of adequate antibiotics and drugs that modulate inflammatory and pro-coagulant response (Dellinger, P. et al., Crit. Care Med. 32: 858-73, 2004; Bernard, G., Vincent, J. L., Laterre, P. F. et al., Efficacy and Safety of Recombinant Human Activated Protein C for Severe Sepsis, N. Eng. J. Med. 344: 699-609, 2001; Bernard, G. R., Margolis, B. D., Shanies, H. M. et al., Extended Evaluation of Recombinant Human Activated Protein C United States Trial (ENHANCE US)* Chest. 125: 2206-2216, 2004). However, mortality is still high, and research is being continued with the objective to obtain better therapeutic results. In this sense, remarkable studies have been produced as regards the possibility to activate defensive stress response signals in different tissue cells of septic patients.

Diverse studies have postulated that lymphocyte loss via apoptosis may be responsible for high immunosupression frequently observed in septic patients (Wang, S. D. et al., J. Immunol. 152: 5014-21, 1994). Other types of cells, such as hepatocytes (Rogers, H. W. et. al., J. Immunol. 156: 679-84, 1996), prismatic epithelial cells of the intestinal tract (Hotchkis, R. S. et al., Crit. Care Med. 25: 1298-1307, 1997) and vascular endothelium cells (Haimovitz-Friedman, A. et al., J. Exp. Med. 186: 1832-41, 1997) may also die via apoptosis during the sepsis process. A recent study conducted on patients whose cause of death had been sepsis/septic shock showed that apoptosis systematically occurs in many types of cells, of which lymphoid cells and prismatic epithelial cells of the intestinal tract are particularly vulnerable (Hotchkis, R. S. et al., Crit. Care Med. 27: 1230-517, 1999). For the purposes of this patent, the term "sepsis" shall also mean "septicemia".

There is a need for finding active principles and formulations that reduce mortality caused by sepsis. Surprisingly, the inventors have found that certain combinations of erythropoietin glycoisoforms effectively prevent sepsis, and can also be successfully used in the treatment of septic patients.

BRIEF DESCRIPTION OF THE INVENTION

One aspect of this invention provides a combination of erythropoietin glycoisoforms for the treatment and prevention of sepsis, wherein such glycoisoforms contain sialic acid in quantities of 4, 5, 6, 7, 8, 9, or 10 molecules of sialic acid per erythropoietin molecule. Such combination may lack some of such glycoisoforms or may be constituted by different proportions of each glycoisoform. Erythropoietin is human erythropoietin and it may be natural, recombinant, analogues, mutants, mimetics, or fragments of erythropoietins. Such combination of erythropoietin has therapeutic and preventive activity in sepsis.

Another aspect of this patent provides a transgenic erythropoietin-producer cell line that produces and releases into the medium any combination of erythropoietin glycoisoforms, wherein such glycoisoforms may contain sialic acid in quantities of, for instance, 4, 5, 6, 7, 8, 9, or 10 molecules of sialic acid per molecule of erythropoietin. Such combination may lack some of such glycoisoforms or may be constituted by different proportions of each glycoisoform. Erythropoietin is human erythropoietin and it may be natural, recombinant, analogues, mimetics, mutants, or fragments of erythropoietins. Preferably, the line cell is a CHO line cell and, moreover, the line cell is preferably the AB2H52 line cell deposited at the DSMZ (Deutsche Sammlung von Mikroorganismen und Zellkulturen), under access number DSM ACC2727. The produced and purified combination of erythropoietin has therapeutic activity as an agent for the treatment and prevention of sepsis.

Another aspect of this invention provides a pharmaceutical composition for the treatment and prevention of sepsis, wherein such composition comprises an active principle constituted by a combination of erythropoietin glycoisoforms, wherein such glycoisoforms contain sialic acid in quantities of 4, 5, 6, 7, 8, 9, or 10 molecules of sialic acid per molecule of erythropoietin and excipient, in adequate quantities. Such combination may lack one or more of such glycoisoforms or may be constituted by different proportions of each glycoisoform. The erythropoietin is human erythropoietin and it may be natural, recombinant, analogues, mimetics, mutants, or fragments of erythropoietins. Such composition may comprise any excipient known in the art of medicine manufacture.

Another aspect of this invention provides a procedure to obtain a determined profile of erythropoietin glycoisoforms. The procedure comprises the following stages:
  a. Cultivation in a culture medium of the AB2H52 cell line deposited at the DSMZ (Deutsche Sammlung von Mikroorganismen und Zellkulturen), under access number DSM ACC2727; and
  b. Purification and isolation of the combination of erythropoietin glycoisoforms, wherein the cell line may be cultivated in a medium containing additives such as N-acetyl-glucosamine, ammonium chloride, sodium chloride, or combinations thereof, and wherein the purification and isolation stage of the combination of erythropoietin glycoisoform is performed through at least one chromatographic stage. The erythropoietin combination comprises a 4.0 to 5.3 isoelectrical point profile. Preferably, the culture medium osmolality ranges from 310 to 450 milliosmol/kg solvent.

Another aspect of this patent provides a procedure to obtain a cell line that produces a combination or erythropoietin glycoisoforms, wherein such glycoisoforms comprise a quantity of sialic acid of 4, 5, 6, 7, 8, 9, or 10 molecules of sialic acid per molecule of erythropoietin. Such combination may lack some of such glycoisoforms or may be constituted by different proportions of each glycoisoform. Erythropoietin is human erythropoietin and it may be natural, mimetics, recombinant, analogues, mutants, or fragments of erythropoietins. The procedure comprises the following stages:
  a. cultivation in a culture medium of a transgenic erythropoietin-producer cell line; wherein the culture medium comprises additives such as N-acetyl-glucosamine, ammonium chloride, sodium chloride, or a combination thereof, and all of them in different proportions;
  b. cloning of the cell line;
  c. determination of the clone that produces such combination; and
  d. purification and isolation of such combination of erythropoietin glycoisoforms. Preferably, the culture medium osmolality ranges from 310 to 450 milliosmol/Kg solvent.

Another aspect of this patent provides a method for the treatment of sepsis that comprises the administration to a mammal in need of an effective quantity of a pharmaceutical composition comprising a combination of erythropoietin glycoisoforms containing sialic acid in quantities of 4, 5, 6, 7, 8, 9, or 10 molecules of sialic acid per molecule of erythropoietin. Such combination may lack some of said glycoisoforms or may be constituted by different proportions of each glycoisoform. Erythropoietin is human erythropoietin and it may be natural, recombinant, analogues, mimetics, mutants, or fragments of erythropoietins. The method may be performed by administering a dose ranging from 10 µg/Kg to 1,000 µg/Kg of the combination of recombinant human erythropoietin glycoisoforms of this invention for a 70-Kg mammal such as an adult person.

Another aspect of this invention provides a method to prevent sepsis that comprises the administration to a mammal in need of an effective quantity of a pharmaceutical composition comprising a combination of erythropoietin glycoisoforms containing sialic acid in quantities of 4, 5, 6, 7, 8, 9, or 10 molecules of sialic acid per molecule of erythropoietin. Such combination may lack some of said glycoisoforms or may be constituted by different proportions of each glycoisoform. The erythropoietin is human erythropoietin and may be natural, recombinant, analogues, mimetics, mutants, or fragments of erythropoietins. The method may be performed by administering a dose ranging from 10 µg/Kg to 1,000 µg/Kg of the combination of the erythropoietin of this invention for a 70-Kg mammal.

Another aspect of this invention provides the use of a combination of erythropoietin glycoisoforms for the prevention and treatment of sepsis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2.

FIG. 3.

FIG. 4: This figure shows the survival curve of mice with experimentally induced sepsis. One hour before double caecal ligation and puncture (CLP), the animals received doses of 5 µg/Kg, 15 µg/Kg, or 30 µg/Kg either of the combination of EPO glycoisoforms of the invention or placebo (control).

FIG. 5: This figure shows survival curves of mice with experimentally induced sepsis. One hour before CLP, the animals received doses of 15 µg/Kg, 30 µg/Kg, or 50 µg/Kg either of commercial EPO (EPREX®, Cilag-Jansen) or placebo (control).

FIG. 6: This figure shows survival curves of mice with experimentally induced sepsis. One hour before CLP, the animals received doses of 15 µg/Kg, 30 µg/Kg, or 50 µg/Kg either of asialo-EPO (EPREX®, Cilag-Jansen) or placebo (control).

DETAILED DESCRIPTION OF THE INVENTION

For purposes of this patent application, the term "the erythropoietin of the invention" shall always refer to a group or combination of erythropoietin glycoisoforms.

An erythropoietin glycoisoform is defined as an erythropoietin that has a single isoelectric point (pI). The diverse glycoisoforms have the same amino acid sequence, but their pI's differ.

According to this invention, transgenic eukaryotic cell lines are provided, preferably transgenic cell lines expressing erythropoietin, particularly a combination of erythropoietin glycoisoforms comprising glycoisoforms containing from 4 molecules of sialic acid per molecule of erythropoietin to glycoisoforms containing 10 molecules of sialic acid per molecule of erythropoietin. For instance, glycoisoforms containing 4, 5, 6, 7, 8, 9, and/or 10 molecules of sialic acid per molecule of erythropoietin.

As an example, the eukaryotic cell line may be, among others, mammals cell lines such as CHO, Vero, MDCK lines; preferably, the eukaryotic cell line is the CHO line and, most preferably, it is the AB2H52 transgenic cell line deposited at DSMZ (Deutsche Sammlung von Mikroorganismen und Zellkulturen), under access number DSM ACC2727, pursuant to the Budapest Treaty dated Jun. 22, 2005.

Regarding the amino-acids skeleton, the erythropoietin produced by the cell line of the invention includes, without limitation, erythropoietin muteins such as those with altered amino acids in the carboxi-end terminal (see U.S. Pat. No. 5,457,089, which is incorporated by reference in its entirety herein), analogues; peptides that attach to the receptor; small molecules that mimetize the erythropoietin that are referred to in this application as mimetics (U.S. Pub. Applic. No. 2002/0016350, which is incorporated by reference in its entirety herein); natural erythropoietin; mutants such as, for instance, those modified in order to reduce their immunogenicity (U.S. Pub. Applic. No. 2004/0063917, which is incorporated by reference in its entirety herein), or modified in order to increase their activity (U.S. Pub. Applic. No. 2004/0091961, which is incorporated by reference in its entirety herein); conjugated (U.S. Pub. Applic. No. 2004/0266690, which is incorporated by reference in its entirety herein). The experts in this art know that for purposes of this invention erythropoietin could be produced with any amino acids skeleton provided that the cell line produced glycoisoforms containing from 4 to 10 molecules of sialic acid per molecule of erythropoietin. For instance, the erythropoietin amino acids skeleton can be SEQ ID NO. 1.

Figure 1:
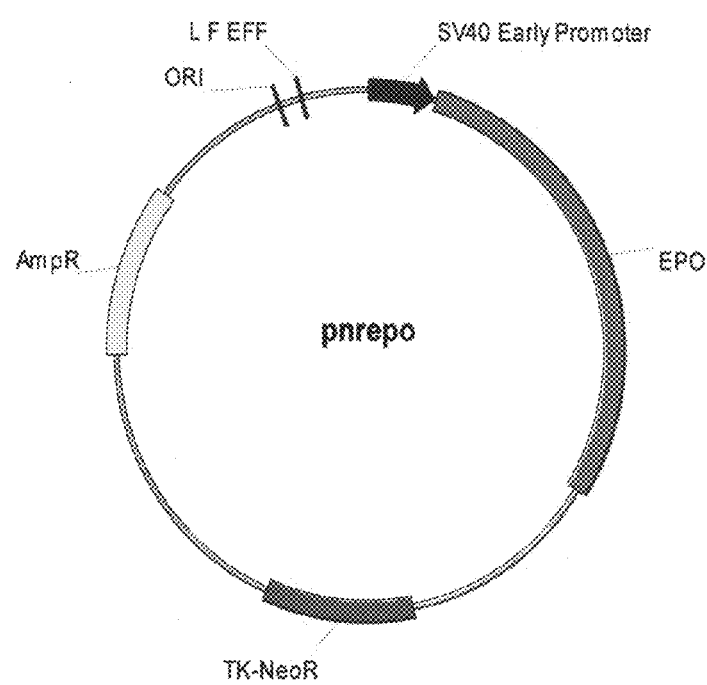
FIG. 1: This figure shows the plasmid restriction map used in the transfection of the CHO.K1 cell line.

The cell line of this invention was obtained by transfecting CHO.K1 cells with the plasmid shown in FIG. 1. The cells selected from culture that produced erythropoietin were cloned and the produced combination of glycoisoforms was assessed by isoelectrofocusing-Western Blot followed by a densitometry study of bands.

In order to displace the glycoisoforms profile toward that of glycoisoforms with lower contents of sialic acid, the selected clones were cultivated in different conditions. The presence of N-acetyl-glucosamine in the culture medium increased the percentages related to less acidic glycoisoforms. On the other hand, the addition of ammonium chloride 2.5 mM also displaced the glycoisoforms profile toward the less acidic ones, and finally the addition of sodium chloride 50 mM in the culture medium also produced the desired displacement. Any expert in this art knows that other types of sodium chloride salts can be used as long as the culture medium osmolality value is maintained between 310 and 450 milliosmol/Kg solvent.

In a preferred embodiment, the cell line of this invention can be obtained by selecting the clones that produce the combination of erythropoietin glycoisoforms of the invention. In another preferred embodiment, the cell line selected can be cultivated in presence of ammonium chloride, sodium chloride, N-acetyl-glucosamine, or combinations of them, to induce the production and release of the combination of erythropoietin glycoisoforms of the invention (glycoisoforms 4 to 10 combined in different proportions, wherein the combination of one or more glycoisoforms may be absent). For instance, the combination of glycoisoforms may comprise a quantity ranging from 2% to 12% of glycoisoform 4, from 5% to 25% of glycoisoform 5, from 9% to 34% of glycoisoform 6, from 9% to 34% of glycoisoform 7, from 10% to 35% of glycoisoform 8, from 2% to 23% of glycoisoform 9, and from 0% to 2% of glycoisoform 10.

Figure 2A:
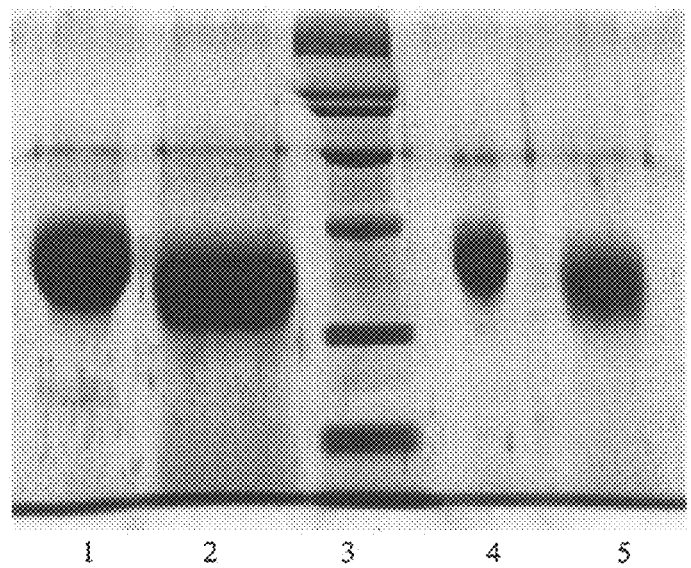
FIG. 2A shows an SDS-PAGE dyed with Coomassie Blue.
Figure 2B:
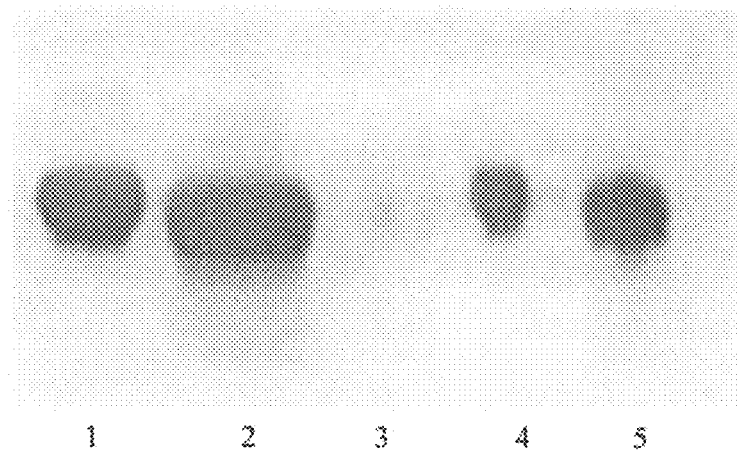
FIG. 2B shows Western Blot bands resulting from the applied gel as shown in FIG. 2A.
Figure 2C:
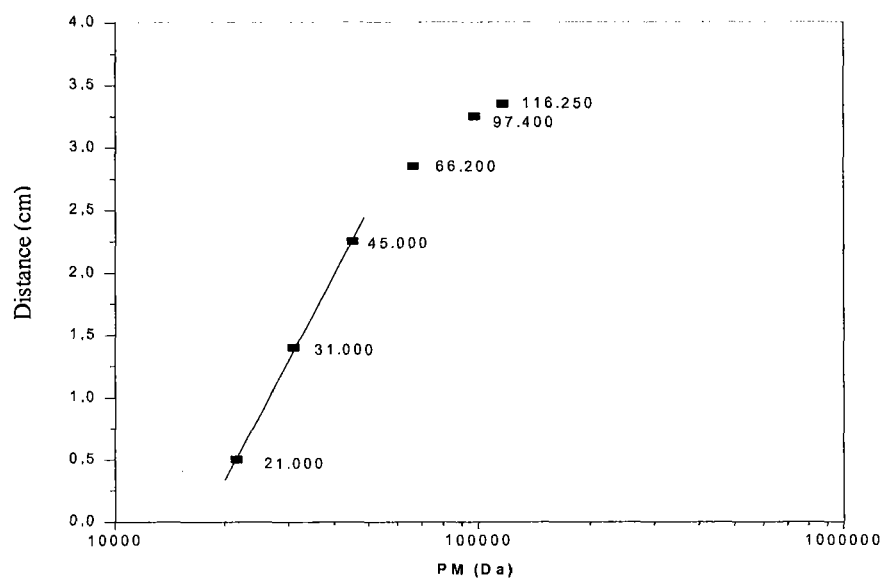
FIG. 2C is the graphic representation of the distance migrated by each molecular weight (MW) pattern as a function of the MW logarithm. In A, B, and C, strand 1 corresponds to 25 µg of commercial EPO (EPREX®, Cilag-Jansen); strand 2 corresponds to 25 µg of the erythropoietin of this invention, strand 3 corresponds to MW patterns (BioRad, USA), strand 4 corresponds to 5 µg of commercial EPO (EPREX®, Cilag-Jansen), strand 5 corresponds to 5 µg of the erythropoietin of this invention.

In a comparative study, the apparent molecular weights of the erythropoietin of the invention and of the commercial erythropoietin (EPREX®, Cilag-Jansen) were calculated. As it can be observed in FIG. 2C, the commercial standard EPO MW is 35,500 Da, and the MW of the erythropoietin of the invention is 33,300 Da. This reduction in the molecular weight might be due to the lower average content of sialic acids in the erythropoietin of the invention.

Figure 3A:
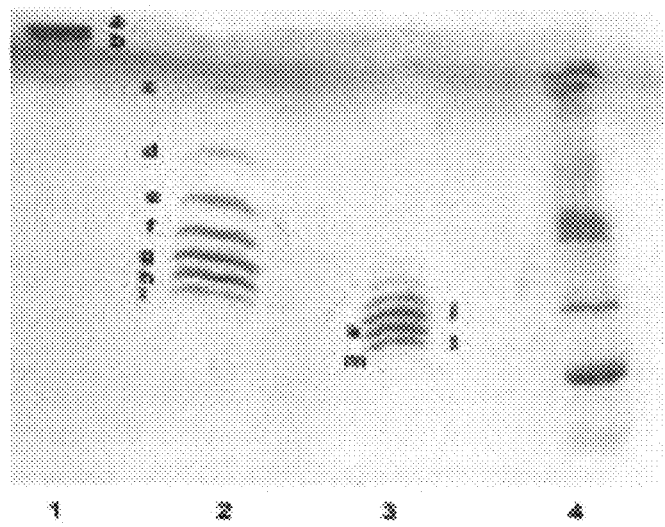
FIG. 3A shows the isoelectrofocusing test bands dyed with Coomassie Blue. Strand 1 corresponds to asialo-EPO, strand 2 corresponds to the erythropoietin of this invention, strand 3 corresponds to commercial erythropoietin (EPREX®, Cilag-Jansen), and strand 4 corresponds to pI patterns (GE Healthcare, Sweden).
Figure 3B:
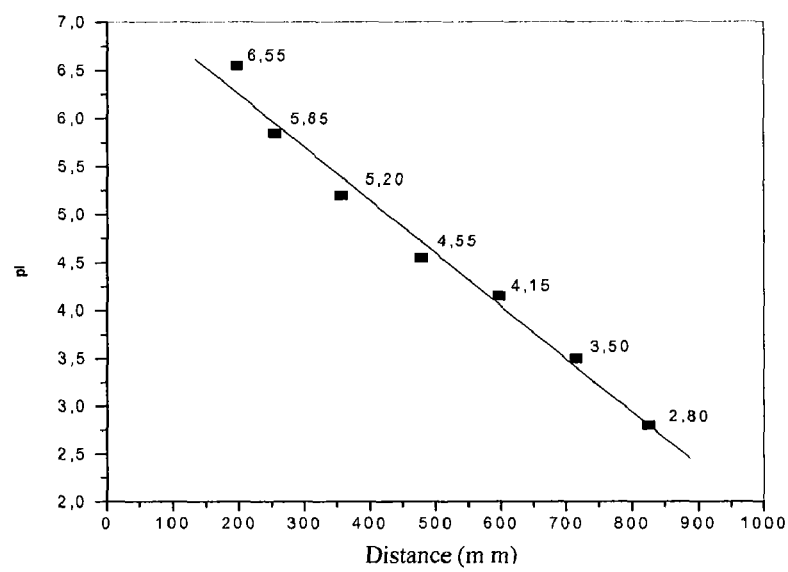
FIG. 3B is a graphic representation of the pI as a function of the migration distance of each pI obtained.

In another comparative study, the isoelectric points (pI's) of the erythropoietin of the invention, asialo-erythropoietin, and commercial erythropoietin (EPREX®, Cilag-Jansen) were determined. As shown in FIG. 3A, the asialo-erythropoietin strand (1) only shows bands "a" and "b" corresponding to 6.7 and 6.6 pI's respectively. Strand 2, wherein the erythropoietin of the invention was seeded, shows the bands from c to i corresponding to pI's 4.0 to 5.3. Strand 3, wherein the commercial EPO was seeded, shows bands from j to m corresponding to PI's 3.5 to 4.3.

From the studies performed, it is concluded that the average contents of sialic acid measured according to European Pharmacopoeia are as follows:

Erythropoietin of the invention: 7.6 mol sialic acid/mol polypeptide.

Asialo-EPO: 4.4 mol sialic acid/mol polypeptide.

Commercial EPO (EPREX®, Cilag-Jansen): 11.3 mol sialic acid/mol polypeptide.

The pI, percentages and sialic acid content of each glycoisoform of the invention were determined by isoelectrofocusing technique (Table 1). The sialic acid content of each glycoisoform is shown in the following table:

TABLE 1

| Band | pI | % | Mol sialic acid/Mol erythropoietin of the invention |
|---|---|---|---|
| 4 | 5.21 ± 0.07 | 6.2 ± 2.2 | 4 |
| 5 | 4.90 ± 0.08 | 14.5 ± 3.0 | 5 |
| 6 | 4.66 ± 0.11 | 21.4 ± 2.9 | 6 |
| 7 | 4.47 ± 0.08 | 21.9 ± 1.7 | 7 |
| 8 | 4.26 ± 0.06 | 22.3 ± 2.5 | 8 |
| 9 | 4.14 ± 0.04 | 13.2 ± 1.2 | 9 |
| 10 | 4.04 ± 0.05 | 0.7 ± 0.2 | 10 |

The combination of the invention may comprise any proportion of glycoisoforms of each of the glycoisoforms 4, 5, 6, 7, 8, 9, and 10; and all of them combined in different ways are within the scope of this invention. In the combination of the invention one or more of the glycoisoforms could be absent, or the proportion of each glycoisoform in the combination could be different. All these variations are within the scope of this invention.

Comparative studies were performed to evaluate the biological activities of the erythropoietin of the invention, commercial erythropoietin (EPREX®, Cilag-Jansen), and asialo-erythropoietin. As shown in Table 2, the in vitro erythropoietic activity of the erythropoietin of the invention is intermediate as compared to those of asialo-EPO and commercial EPO ones.

TABLE 2

| Sample | IU/mg |
|---|---|
| Commercial EPO | 120,000 |
| Preparation of the invention | 179,908 |
| Asialo-EPO | 623,743 |

However, the in vivo hematopoietic activity of the preparation of this invention that was measured in normokinetic mice according to European Pharmacopoeia is remarkably inferior to that of commercial EPO (Table 3).

TABLE 3

| Preparation | Specific Erythropoietic Activity (IU/mg) |
|---|---|
| EPO of the invention | 6,180 |
| Commercial EPO | 120,000 |

In order to compare the plasma half-lives of the erythropoietin of the invention, the asialo-EPO, and the commercial EPO (EPREX®, Cilag-Jansen), in vivo tests were performed on Wistar rats. The results of the plasmatic clearance are shown in Table 4. As expected, the plasmatic clearance of the erythropoietin of the invention is intermediate as compared to that of commercial EPO, which is more acidic, and that of the asialo-EPO.

TABLE 4

| Preparation | Plasmatic Clearance (minutes) |
|---|---|
| Preparation of the invention | 27.5 |
| Commercial EPO | 134.0 |
| Asialo-EPO | 1.8 |

Afterwards, a study was performed on the preventative effect of the preparation of the invention on the survival of septic mice, among which infection was induced by CLP (caecum ligation and puncture) technique. It was observed that the erythropoietin of the invention reduced mortality when administered in doses of 15 μg/Kg, 30 μg/Kg, and 50 μg/Kg (FIG. 4) (p=0.02, 0.03, and 0.01, respectively) (Logrank Test).

None of the Sham group animals died (definition: Sham group refers to animals on which a simulated surgery was performed in order to evaluate surgical stress).

Unlike commercial erythropoietin, the combination of EPO glycoisoforms of the invention can be used at higher doses without causing a thrombopoietic effect.

Commercial EPO (EPREX®, Cilag-Jansen) reduced mortality when administered at a dose of 15 μg/Kg (FIG. 5). However, at higher doses, commercial EPO was not as effective and increased mortality, probably due to the damage caused by the erythropoiesis increase and its consequent thrombopoietic effect.

Asialo-EPO did not reduce mortality in all studied doses (FIG. 6).

The application of erythropoietin may prevent or be useful in the treatment of sepsis as long as such erythropoietin is not asialo-EPO.

As described in this patent, any combination of erythropoietin glycoisoforms or a single glycoisoform is useful for the treatment and prevention of sepsis, septic shock and other disorders, such as severe hypovolemic shock or cardiogenic-related shock, and other non-infectious causes, such as multiple trauma, pancreatitis, severe burns and disorders caused by toxic agents, hypoxia, ischemia, or necrosis, among others.

In a preferred embodiment, the combination of glycoisoforms for the treatment and prevention of sepsis is the combination that comprises glycoisoforms of 4, 5, 6, 7, 8, 9, or 10 molecules of sialic acid per molecule of erythropoietin. More preferably, it is the combination of glycoisoforms that releases the cell line of this invention into the culture medium.

Figure 7:
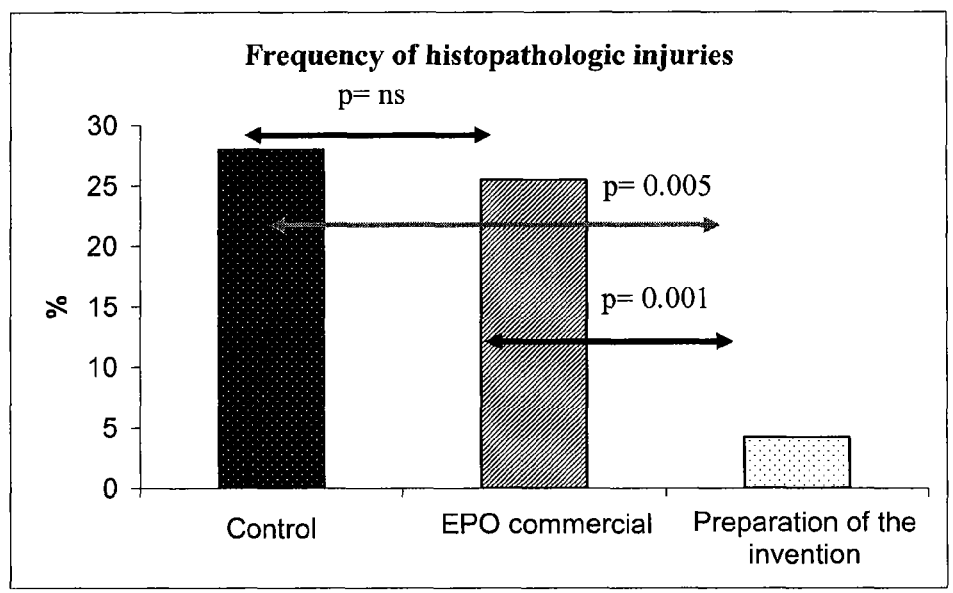
FIG. 7: This figure shows the frequency of general histopathologic lesions in septic mice preventatively treated with 50 µg/Kg of commercial EPO or with 50 µg of the EPO combination of the invention.

On the other hand, the treated animals' multi-organ damage (MOD) was studied. FIG. 7 shows that the combination of glycoisoforms of the invention drastically reduced the incidence of serious histopathologic injuries associated with sepsis (4.2% vs. Control 28% p=0.001), whereas that benefit was not observed in the case of administration of commercial EPO (commercial EPO 25.5% vs. Control 28% p=NS). Table 5 shows that the incidence of serious renal damage (intense congestion, acute tubular necrosis or focal renal necrosis) was as follows: Control: 28.5%, commercial EPO: 14.2%, combination of the EPO of the invention: no renal damage was observed. 25% of the control group, 37.5% of the commercial EPO group, and 12.5% of the group of animals treated with the EPO combination of the invention presented hepatic compromise (intense congestion or necrosis).

No renal damage was observed in the group of animals treated with the EPO of the invention, whereas 42.8% of the control group animals and 37.5% of the animals treated with commercial EPO presented intestinal necrosis or apical lysis. 25% of the animals, both in the control group and in the commercial EPO group, and 12.5% of the animals treated with the EPO combination of this invention had sepsis-related lung damage (necrosis, intra-alveolar or hemorrhagic congestion).

The animals treated with the combination of glycoisoforms of this invention had no cardiac damage, whereas 37.5% of the control group and 25% of the commercial EPO group animals presented myocardial damage. No mouse had cerebral damage, except for one animal in the control group that presented inflammatory infiltrate.

TABLE 5

Histopathologic injuries in organs of animals that survived from experimental sepsis.

| Control Group | | | | | | |
|---|---|---|---|---|---|---|
| Day | Liver | Kidney | Intestines | Lungs | Heart | Brain |
| 1 | Intense Congestion | Intense Congestion | Necrosis | Congestion | Congestion | Congestion |
| 2 | S/P | Congestion | Lymphoid hyperplasia | Hemorrhagic Congestion | Congestion | S/P |
| 3 | Necrosis | Congestion | NO | Hemorrhagic Congestion | Congestion | S/P |
| 4 | Congestion | Intense Congestion | S/P | S/P | S/P | S/P |
| 4 | Congestion | NO | Necrosis Lymphoid hyperplasia | Congestion | S/P | S/P |
| 5 | Congestion | S/P | Apical Lysis | S/P | S/P | S/P |
| 5 | Edema | S/P | Lymphoid hyperplasia | S/P | S/P | S/P |
| 6 | Hematopoiesis | S/P | S/P | S/P | S/P | S/P |

| Group of animals treated with commercial EPO | | | | | | |
|---|---|---|---|---|---|---|
| Day | Liver | Kidney | Intestine | Lungs | Heart | Brain |
| 1 | Intense Congestion | Intense Congestion | Lymphoid hyperplasia | Intense congestion | Congestion | NO |
| 2 | Necrosis | NO | Diffuse necrosis | Intense congestion | Congestion | S/P |
| 3 | Necrosis | Congestion | Necrosis | Congestion | S/P | S/P |
| 3 | Congestion | Septic embolism | Edema | Congestion | Septic embolism | S/P |
| 4 | Congestion | S/P | S/P | S/P | S/P | NO |
| 4 | S/P | S/P | S/P | S/P | S/P | S/P |
| 4 | S/P | S/P | Lymphoid hyperplasia | S/P | S/P | NO |

TABLE 5-continued

Histopathologic injuries in organs of animals that survived from experimental sepsis.

| | | | | | | |
|---|---|---|---|---|---|---|
| 5 | Edema | S/P | Apical Lysis | Congestion | S/P | NO |

Group of animals treated with the combination of glycoisoforms of this invention

| Day | Liver | Kidney | Intestine | Lungs | Heart | Brain |
|---|---|---|---|---|---|---|
| 1 | Intense congestion | Congestion | S/P | Intense congestion | S/P | S/P |
| 2 | S/P | S/P | S/P | S/P | S/P | S/P |
| 3 | S/P | S/P | S/P | S/P | S/P | S/P |
| 3 | Congestion | S/P | S/P | S/P | S/P | S/P |
| 4 | S/P | S/P | S/P | S/P | S/P | S/P |
| 5 | Congestion | Congestion | S/P | Congestion | S/P | S/P |
| 6 | Congestion | S/P | S/P | S/P | S/P | S/P |
| 6 | Congestion | Congestion | S/P | S/P | S/P | S/P |

These results clearly show that the combination of EPO glycoisoforms of this invention is useful for the prevention of multi-organ damage and death caused by sepsis.

Figure 8:
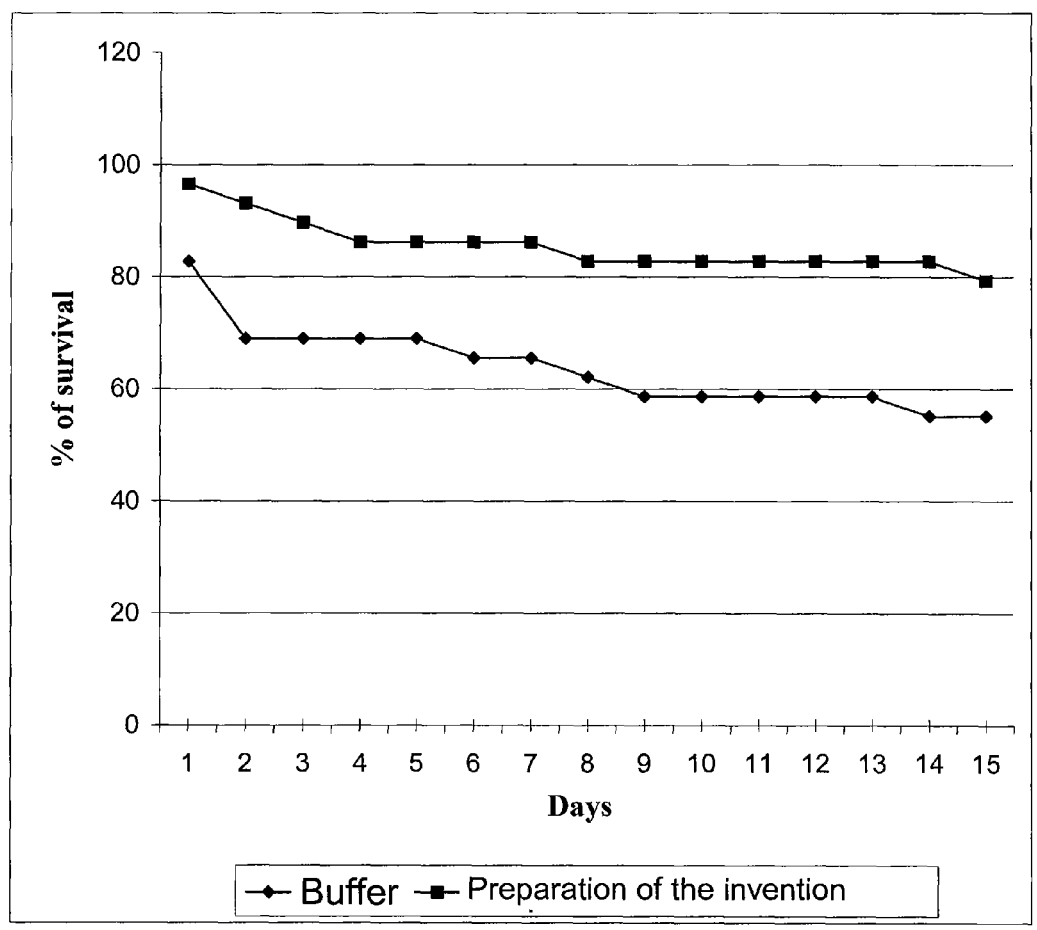
FIG. 8: This figure shows survival curves of mice with experimentally-induced sepsis. One hour after CLP, the animals received doses of 15 µg/Kg, 30 µg/Kg, or 50 µg/Kg either of the combination of EPO glycoisoforms of the invention or of placebo (control).

In order to verify whether the preparation of the invention is also useful to prevent death caused by sepsis once it is established, experimental sepsis was induced in mice by the CLP technique. It was observed that the combination of glycoisoforms of this invention significantly reduced mortality when administered in a dose of 50 µg/Kg 1 hour after CLP (FIG. 8). Therefore, the preparation of the invention is also useful to enhance survival when the treatment is applied post-sepsis.

The invention also comprises a pharmaceutical composition for the treatment of sepsis or other related disorders. In a preferred embodiment, the pharmaceutical composition for the treatment or prevention of sepsis comprises diverse combinations of erythropoietin glycoisoforms, such as a combination of glycoisoforms containing 4, 5, 6, 7, 8, 9, or 10 molecules of sialic acid per molecule of erythropoietin, in which one or more glycoisoforms may be absent in said combination, or it may contain different proportions of each glycoisoform. More preferably, it is the combination of glycoisoforms, as well as known state-of-the-art excipients, released by the cell line of this invention into the culture medium.

The pharmaceutical composition of the invention may be manufactured, for example, in the form of pills, tablets, capsules, particles; sublingual, intranasal, or injectable solutions, or other forms known in this art, all of them falling within the scope of this invention.

As a non-limiting example, the pharmaceutical composition of this invention may comprise 400.00 µg/Kg of the erythropoietin of the invention per 1 mL of injectable solution; human albumin, 1.2 mg of monobasic sodium phosphate monohydrate; 1.8 mg of anhydrous dibasic sodium phosphate; 0.7 mg of sodium citrate; 5.8 mg of sodium chloride; and 6.8 mg of citric acid in USP water for injectables (pH 6.9±0.3).

As regards the use of the combination of EPO glycoisoforms of the invention, such combination can be applied at higher concentrations than commercial EPO glycoisoforms for the treatment or prevention of sepsis or other related disorders without causing effects such as erythropoiesis increase. On the other hand, the application of asialo-EPO is barely useful for the treatment of sepsis.

This invention is better illustrated in the following examples, which should not be interpreted as an imposed limitation to this invention. On the contrary, it must be clearly understood that it is possible to turn to other embodiments, modifications and equivalents of this invention that the experts in this matter may suggest after reading this description as long as such suggestions do not divert from the spirit of this invention and/or the scope of the attached claims.

EXAMPLES

Example 1

Obtaining an Erythropoietin-Producer Cell Line

The cell line used was CHO.K1 (ATCC CCL-61). For the growth and maintenance stages the culture medium used was the so-called Medium 1 (composed of a 1:1 mixture of the D-MEM (Gibco) and Ham's F12 (Gibco) mediums supplemented with sodium bicarbonate (Gibco) 2.441 g/l, D (+) anhydrous glucose (Sigma) 1.183 g/l, sodium pyruvate (Gibco) 0.11 g/l, glutamine (Sigma) 1.10 g/l, tryptophan (Sigma) 0.027 g/l, aspartic acid (Sigma) 0.04 g/l, serine (Sigma) 0.080 g/l, bovine fetal serum (BFS) (Bioser) 8% V/V, and gentamicin (Gibco) 50 µg/ml.

The cells were transfected with the plasmid called pnrepo (FIG. 1), obtained by cloning the human erythropoietin gene in the commercial plasmid pClneo with eukaryotic expression.

The transfected cells were selected by using the antibiotic neomycin, and the producer cells were analyzed by using the ImmunoDot test.

The cell lines showing a high production level of erythropoietin were cloned by the limiting dilution method. The best producing clones were selected by means of ImmunoDot, and the erythropoietin isoform pattern produced by each of such selected clones was analyzed.

Example 2

Evaluation of the Glycosialation Pattern of the Produced Glycoisoforms

The glycoisoform pattern produced by each clone was studied by means of isoelectrofocusing Western Blot, followed by band densitometry. The isoelectric focusing was performed by means of a MULTIPHOR® II (GE Healthcare) device.

The electrophoretic support was prepared by using an 8% (w/v) acrylamide/bisacrylamide concentration with the addition of 7 M urea and ampholytes to generate a 3-10 pH range.

Prefocusing of ampholytes was performed for 1 hour using 2,000 V-100 mA-10 W, at 10° C. Afterwards, 20 µl (20 µg) of samples of the EPO glycoisoforms were partially purified from the supernatants of the selected clones. Focusing was performed for 30 minutes under the same conditions.

After isoelectric focusing, the gel was dyed with Coomassie Blue solution, or, alternatively, the glycoisoforms were transferred to nitrocellulose membranes. Transference was performed for 1 hour at room temperature.

Finally, the presence of EPO glycoisoforms was detected in the nitrocellulose membranes by means of a specific immunochemical reaction. The clones showing a glycoisoform pattern with predominance of glycoisoforms with lower sialic acid content were selected, and a displacement towards glycoisoforms with lower sialic acid content was performed.

Example 3

Obtaining Clones of Erythropoietin-Producer Cells with Low Sialic Acid Content

In order to obtain clones producing a human erythropoietin glycoisoform profile displaced towards those containing a low quantity of sialic acid, the clones selected in Example 2 were cultivated under different conditions
a) In 6 SMIF medium with the addition of 20 mM N-acetylglucosamine (GlcNAc).
b) In 6 SMIF medium with the addition of 2.5 mM of $NH_4Cl$.
c) In 6 SMIF medium with the addition of 50 mM of NaCl.

The glycoisoforms glycosialation pattern was evaluated by using the methods described in Example 2, and the clones producing a glycoisoform pattern with low sialic acid content were selected.

Example 4

Enrichment and Purification of Human Erythropoietin Glycoisoforms with Lower Content of Sialic Acid At an initial stage, the culture supernatant was filtrated in cartridges with 3-0.8 µm size pores and sequentially in cartridges with 0.8-0.45 µm size pores (Pall Technology, USA), applying a pressure inferior to 0.5 $kgf/cm^2$. The filtrated harvest was immediately processed.

Afterwards, a volume of 18 liters of the filtrated medium was applied to a BPG 100/500 (10×12.7 cm) column that contained 1 liter of Blue-SEPHAROSE® Fast Flow (GE Healthcare) with previous 50 mM phosphate pH 7 balance at a variable 11-27 ml/minute flow. This methodology enabled the seizure of all EPO glycoisoforms present in the culture supernatant.

The column was washed later with balance buffer, using a 4-7 column-volume (CV) solution. All the absorbed EPO glycoisoforms were recovered by using a 2.5-4 CV solution composed of NaCl 675 mM, 20% ethanol (v/v), Tris 20 mM pH 6.5 at a 44-67 ml/minute flow. The column was exhaustively washed using MilliQ-quality water and kept in a 20% ethanol solution (v/v). The product of the elution concentrated up to a volume ranging from 75 to 100 ml and a buffer change was performed with Tris 20 mM pH 6.5 solution, using a PELLICON® (Millipore, USA) tangential ultrafiltration system with cartridges of 10 kDa size pore and 0.1 $m^2$ surface. The product was then diafiltered using 10 times the concentrated volume. The resulting product was either kept at −20° C. or immediately processed.

From 2.1 to 6.2 liters of the product obtained at the previous stage were applied to a BPG 100/500 (10×14 cm) column containing 1.1 liter of Q-SEPHAROSE® Big Bead (GE Healthcare) previously balanced with a Tris 20 mM ph 6.5 solution at 25 ml/minute flow. It was washed with 1.5-2.5 CV balance buffer. The least acidic EPO glycoisoforms were recovered by using 3-4 CV of 50 mM glycine solution.

The 50 mM glycine solution was taken to pH 5 by adding 1 M pH 5 acetate buffer and a NaOH 10 N solution. A volume of 2 to 3 liters of sampling was applied to a XK 50/20 (2.5×5 cm) column containing 50 ml of Q-SEPHAROSE® Fast Flow (GE Healthcare) previously balanced in 20 mM pH 5 acetate buffer at 25 ml/minute flow.

Two washings were performed—one with 5 CV of 20 mM pH 5 acetate buffer, and another with 1 CV of 20 mM pH 6.5 citrate buffer. The least acidic EPO glycoisoforms were recovered with a NaCl 100 mM solution in 20 mM pH 6.5 citrates, thus collecting 7 column volumes. Workflow was constant throughout the whole experience.

Example 5

Characterization of the Erythropoietin of the Invention a) Determination of Molecular Weight:

The apparent molecular weight of the different EPO samples purified according to example 4 was determined through polyacrylamide gel electrophoresis in the presence of SDS (SDS-PAGE) and a disulphide bond-reducing agent (beta-mercaptoethanol). Electrophoresis was basically performed following the method described by Laemmli (Laemmli, U.K., 1970, *Cleavage of structural proteins during the assembly of the head of bacteriophage $T_4$*. Nature 227: 680-685, included in this patent as reference) using the MINI PROTEAN® II (Bio Rad, Calif., USA) modular electrophoresis system.

For this purpose, samples of EPO (25 µg) were re-suspended in a solution of 50 mM Tris-HCl, 2% SDS (w/v), 10% glycerol (v/v), 5% β-ME (v/v), 0.05% bromophenol blue (w/v), pH 6.8. The samples were incubated at 100° C. for 3 minutes and applied onto a 5% acrylamide/bisacrylamide concentration (w/v) stacking gel. The separation gel was polymerized with a 12% acrylamide/bisacrylamide concentration (w/v). Simultaneously, molecular weight markers (Bio-Rad) were seeded with the purpose of determining the apparent molecular weight of the studied samples. The electrophoretic run was performed at constant voltage (200 V) until the run front reached 0.5 cm from the inferior border of the separation gel.

Finally, the gel was stain-dyed with Coomassie Brilliant Blue by a 10-minute submersion in a solution composed of 0.1% Coomassie R-250 (w/v) in 40% methanol (v/v) and 10% acetic acid (v/v). Gel was discolored by using a solution composed of 7.5% methanol (v/v) and 5% acetic acid (v/v) until clear bands revealed against a completely destained background.

The apparent molecular weight was determined by interpolation of the distance migrated by each sample in a graphic representation of the distance migrated by each marker according to its molecular weight.

b) Determination of the Isoelectric Point

The apparent isoelectric point of each different EPO sample was determined by using gel isoelectrofocusing technique with the MULTIPHOR® 11 (GE Healthcare, Sweden) system.

The electrophoretic support was prepared using an 8% concentration (w/v) acrylamide/bisacrylamide mix with the addition of 7 M urea and ampholytes to generate a 3-10 pH gradient. The gel was pre-focused at 2,000 V-100 mA-10 W for 1 hour. Afterwards, 20 µg of the various EPO preparations were seeded in a 20 µl volume, then proceeding with the focusing for 40 minutes under the same aforementioned conditions. Isoelectric point markers (GE Healthcare) were seeded as controls.

Once the isoelectrofocusing was finished, the gel was colored with Coomassie Brilliant Blue, and then subjected to discoloration until getting clear bands against a completely destained background. The apparent isoelectric point was determined by interpolation of the distance migrated by each sample in a graphic representation of the distance migrated by each marker as a function of its isoelectric point.

Example 6

In Vitro Analysis of the Erythropoietin Biological Activity

Biological activity was performed in a proliferation test using TF-1 cells.

Culture mediums used:

Growth medium: 500 ml of RPMI 1640 (Gibco, USA) medium, 5 ml of 200 mM L-Glutamine (Fluka, Germany), 0.75 g of $NaHCO_3$ (Gibco, USA), 50 µg/ml of gentamicin (Parafarm, Argentina), sterilized by filtration through 0.22-µm pore filters; supplemented with 10% v/v of bovine fetal serum (BFS) (Bioser, Argentina), 5 ml of 5 mM β-mercaptoethanol (Merck, Germany), and 5 ng/ml of rhGM-CSF (Growgen, Bioprofarma S.A., Argentina).

Test medium: Growth culture medium lacking rhGM-CSF.

Washing medium: Growth culture medium lacking rhGM-CSF and SFB.

A suspension of TF-1 cells in logarithmic growth phase was used. The cells were washed with 30 ml of the washing medium 3 times. Then, the cells were re-suspended in the test medium in a concentration of 200,000 cell/ml, and incubated at 37° C. for 2 hours. Finally, 50 µl of the cell suspensions were seeded in each cavity of a 96-wells plate (except for the wells corresponding to the color reagent control) and the following were added: 50 µl of the erythropoietin of the invention purified according to Example 4; 50 µl of a commercial erythropoietin (EPREX®, Cilag-Jansen) (7,500 mU/ml) in serial dilutions in the medium so as to have curve concentration variations ranging from 15 to 2,000 mU/ml; 50 µl of asialo-EPO; and 50 µl of test medium, as the case may be. The plates were incubated at 37° C. for 72 hours.

The tested controls were performed according to the following detail:

positive control: 50 µl of test medium, supplemented with 7,500 mU/ml of EPO.

negative control: 50 µl of test medium.

color reagent control: only 100 µl of medium test were placed.

Finally, 20 µl of coloring solution (2 ml of a 2.0 mg/ml of MTS (Promega, USA) solution, and 100 µl of a 0.92 mg/ml of PMS (Sigma, USA) solution) was added to each cavity. It was incubated at 37° C. and 6 hours later the color developed was read in an ELISA reader at two wavelengths, 492 and 690 nm.

Example 7

Evaluation of Erythropoietin Clearance

18 Wistar strain female rats between 8 and 10 weeks of age and 200 g of weight from the CNEA (National Commission of Atomic Energy of Argentina) biotery were used.

The animals were housed at the FBCB-UNL Cell Culture Laboratory biotery, with free access to water and balanced diet. The sector temperature was kept at 23° C. The lighting regime was 12 hour light/12 hour darkness.

The animals were randomly divided into 3 groups of 6 individuals each. Each group was, in turn, divided in 3 subgroups of 2 animals each. The subgroups were kept in separate cages.

The evaluated preparations were: the preparation of the invention, commercial EPO (EPREX®, Cilag-Jansen) and asialo-EPO.

The asialo-EPO was prepared by mixing commercial EPO (EPREX®, Cilag-Jansen), a sufficient quantity of a buffer provided in the Neuroaminidase-P0720S (New England BioLabs Inc., USA) kit and a sufficient quantity of the neuraminidase enzyme provided in said kit. It was mixed and incubated at 37° C. for 2 hours. Finally, the mixture was dialysed against PBS at 4° C. overnight.

The animals were anesthetized by intramuscular injection of a mixture composed of 140 µl of 50 mg/ml ketamine and 75 µl of 20 mg/ml Xilacine. Once anesthetized, the animals were inoculated an injection in the major tail vein. Each animal was injected 500 µg of the corresponding erythropoietin according to the treatment scheme, in a volume of 500 µg of solution, using tuberculin syringes furnished with 29 g needles.

The animals were bled by puncture of the retro-orbital vein using a heparinized Pasteur pipette. Blood was collected in 15 ml Falcon tubes containing 50 µg of 5,000 IU/ml sodium heparin. The samples were centrifuged at 700 g and at 20° C. in an Eppendorf 5403 (Germany) centrifuge for 20 minutes, and the plasma obtained by this procedure was kept at −20° C.

Blood samples were taken from the animals of each group at 0, 2, 6, 15, 30, and 60 minutes post injection, and at 2, 3, 5, 24, and 30 hours post injection.

Plasma concentrations of the different injected erythropoietins were determined through a sandwich ELISA (Amadeo, I., et al., J. Immunol. Meth. 293: 191-205, 2004, which is incorporated by reference in its entirety herein).

Concentration curves were built versus post-injection time, resulting in the following pharmacokinetic parameters:

Maximum plasma concentration ($C_{max}$) and maximum time ($T_{max}$), corresponding to the time at which the maximum concentration ($C_{max}$) is reached.

Other pharmacokinetic parameters were determined by adjusting the experimental data through a bi-exponential equation for the plasma concentration (C) as a function of time (t), as shown in equation (1):

$$C = A \cdot e^{-\alpha t} + B \cdot e^{-\beta t} \quad (1)$$

where A and α are constants of the initial phase that reflects the erythropoietin distribution in all the animal's intracellular fluids, whereas B and β are constants of the elimination phase that are related to the real plasmatic clearance (Donahue et al., Cold Spring Harbor Symp Qant. Biol. 51: 685-692, 1986, totally included herein as reference). These constants were estimated from the empiric data by use of computer tools (Microcal™ Origin™, 5.0 Version, Microcal Software, USA). The distribution half life time ($T_{1/2}\beta$), the elimination half life time ($T_{1/2}\alpha$), and the total plasmatic clearance (CL) were calculated by using equations (2), (3), and (4), respectively:

$$(T_{1/2}\alpha) = 0.693/\alpha \quad (2)$$

$$(T_{1/2}\beta) = 0.693/\beta \quad (3)$$

$$CL = dose/AC_{0-\infty} \quad (4)$$

where $AC_{0-\infty}$ is the area under the concentration curve as a function of time, from zero to infinity. Differences among the three preparations were evaluated through a Student paired test, taking as most significant probabilities those less than 0.05.

Example 8

Determination of In Vivo Erythropoietic Activity

In order to determine the in vivo erythropoietic activity of each preparation, a test was performed using normocytopenic mice pursuant to European Pharmacopoeia.

Each sample to be analyzed was diluted using a phosphate/albumin pH 7.2 buffer. The buffer was prepared according to the following instructions: dissolve 10.75 g of sodium acid phosphate and 7.6 g of sodium chloride in 900 ml of distilled water; add 5 ml of a concentrated solution of 200 mg/ml human albumin and complete with distilled water csp until reaching a final volume of 1,000 ml. Adjust pH to 7.2 with a solution of diluted sodium hydroxide or diluted phosphoric acid.

Three serial dilutions of order 3 of the sample and of an International EPO Standard were performed in a way in which the International Standard dilutions contained 20, 60 and 180 IU/ml of EPO.

0.5 ml of each dilution of the sample and of the Standard were inoculated in NMRI 2-month old female mice by subcutaneous injections. 6 mice per dilution were used.

4 days later, the mice were anesthetized with sodium pentothal (3 mg/0.5 ml/mouse) and were bled through the retro-orbital sinus using heparinized capillaries. The blood was transferred to EPPENDORF® tubes containing 5 µl of sodium heparin.

Reticulocytes were quantified taking 5 µl of a pH 7.2 reticulocyte buffer. The buffer was prepared according to the following protocol: dissolve 10.75 g of disodium acid phosphate, 7.6 g of sodium chloride, 0.2 g of sodium azide, and 0.74 g of EDTA in distilled water, and then take to a final volume of 1,000 ml. Adjust pH to 7.2.

It was stirred for homogenization purposes, and fluorescent staining was performed by adding 0.5 ml Thiazol orange stain into each tube. It was mixed and left in the dark at room temperature for 30 minutes. Reading was performed using a flowcytometer (Becton Dickinson FACSCalibur P/N 34012420). 60,000 events were read for each sample and the data were processed using the Retic-count program. The data were entered into a statistical program in order to obtain sampling power.

Example 9

Evaluation of the Erythropoietin of the Invention as an Active Principle for the Treatment of Sepsis, and Determination of Adequate Dose Animals: 5-7-week old female Cf1 mice of approximately 25-30 g weight were used.

The animals were housed at the biotery, where they were kept for a minimum period of 7 days to enable their acclimatizing, with free access to water and balanced diet. The sector temperature was kept at 20°±2° C. The lighting regime was 12 hour light/12 hour darkness.

The animals received doses equivalent to 5 µg/Kg, 15 µg/Kg, 30 µg/Kg, and 50 µg/Kg, as applicable to each case according to weight expressed in Kg, of the erythropoietin of the invention, commercial EPO (EPREX®, Cilag-Jansen), and asialo-EPO by subcutaneous injection one hour prior to sepsis induction in the prevention case, or one hour after sepsis induction in the case of sepsis treatment. The control group received similar quantities of physiological solution.

Sepsis was induced using the double caecal ligation and puncture (CLP) experimental sepsis model (Witchterman K A, Baune A E, Chaudry I H., Sepsis and septic shock: a review of laboratory models and a proposal, J. Surg. Res. 29: 189-201, 1980, included in this patent only as reference). As a summary, the animals fasted for 12 hours prior to intervention. In order to prevent hypoglycemia, drinking troughs water was replaced by 10% glucose. The mice were intraperitoneally anesthetized with ketamine/xilazine (133:10 µg/mouse g) (50 mg/ml Holliday® ketamine and 20 mg/ml Narcoxil® xilazine). Afterwards, a minimum medial laparotomy was performed. The caecum was ligated with surgical suture at 1 cm from its distal end, taking care not to obstruct the ileocaecal valve. Two orifices were made with an 18-g needle in the caecum distal to the ligation place. The caecum was compressed to make a little quantity of the enteric content pass through the orifices. The caecum was introduced into the peritoneal cavity and the abdominal wall was closed in two planes. Finally, in order to ensure mice hydration, 1 ml of 0.9% saline solution was applied by subcutaneous injection. From then onwards, all the animals had free access to water and food.

Simulated surgery was performed in one group of animals in order to evaluate the surgical stress (Sham group).

Daily mortality was evaluated for 15 days in mice that recovered from anesthesia.

On day 16, a retro-orbital bleeding with anesthesia was performed on them in order to determine hematocrit and hemoglobin, according to standard methods. Finally, the animals were sacrificed and autopsies were conducted.

Statistical analysis: The survival curves were graphically represented as survival percentages, and comparison calculations among such curves were performed using Logrank test.

Example 10

Multi-Organ Damage Studies

Different groups of animals with sepsis were treated. Some time before the CLP, the first group of animals received 50 µg of commercial EPO (EPREX®, Cilag-Jansen) through subcutaneous injections; the second group, 50 µg of the preparation of the invention; and the third group, 50 µg of physiological solution. The mice were randomly sacrificed within the first six days of CLP. The following organs were evaluated by means of a histopathologic study using the hematoxilyn-eosin technique: brain, heart, lungs, intestines, liver and kidneys. Related damage was established for each organ and each animal according to the histopathologic study. The histopathologic analysis was independently and blindingly performed. Fisher's Exact Test was used to compare the event frequency, and a p<0.05 was considered significant.

Although the invention is illustrated and described herein with reference to specific embodiments, the invention is not intended to be limited to the details shown. Rather, various modifications may be made in the details within the scope and range of equivalents of the claims and without departing from the invention.

The invention claimed is:

1. A combination of erythropoietin glycoisoforms for the reduction of mortality caused by sepsis comprising 6.2+/−2.2% of glycoisoform 4 containing 4 molecules of sialic acid per erythropoietin molecule, 14.5+/−3.0% of glycoisoform 5 containing 5 molecules of sialic acid per erythropoietin molecule, 21.4+/−2.9% of glycoisoform 6 containing 6 molecules of sialic acid per erythropoietin molecule, 21.9+/−1.7% of glycoisoform 7 containing 7 molecules of sialic acid per erythropoietin molecule, 22.3+/−2.5% of glycoisoform 8 containing 8 molecules of sialic acid per erythropoietin molecule, 13.2+/−1.2% of glycoisoform 9 containing 9 molecules of sialic acid per erythropoietin molecule and, optionally, 0.7+/−0.2% of glycoisoform 10 containing 10 molecules of sialic acid per erythropoietin molecule, wherein said combination of erythropoietin glycoisoforms has an isoelectrical point profile between 4 and 5.3 and a molecular weight profile ranging from 32 to 34 kD and wherein said erythropoietin is recombinant human erythropoietin.

2. The combination according to claim 1, wherein said combination of erythropoietin is an agent selected from the group consisting of an active agent for the reduction of mortality caused by sepsis.

3. A pharmaceutical composition for the reduction of mortality caused by sepsis, comprising a combination of erythropoietin glycoisoforms as active agent, wherein said combination comprises 6.2+/−2.2% of glycoisoform 4 containing 4 molecules of sialic acid per erythropoietin molecule, 14.5+/−3.0% of glycoisoform 5 containing 5 molecules of sialic acid per erythropoietin molecule, 21.4+/−2.9% of glycoisoform 6 containing 6 molecules of sialic acid per erythropoietin molecule, 21.9+/−1.7% of glycoisoform 7 containing 7 molecules of sialic acid per erythropoietin molecule, 22.3+/−2.5% of glycoisoform 8 containing 8 molecules of sialic acid per erythropoietin molecule, 13.2+/−1.2% of glycoisoform 9 containing 9 molecules of sialic acid per erythropoietin molecule and, optionally, 0.7+/−0.2% of glycoisoform 10 containing 10 molecules of sialic acid per erythropoietin molecule and acceptable pharmaceutical excipients, wherein said combination of erythropoietin glycoisoforms has an isoelectrical point profile between 4 and 5.3 and a molecular weight profile ranging from 32 to 34 kD and wherein said erythropoietin is recombinant human erythropoietin.

4. The composition according to claim 3, wherein said erythropoietin combination is an agent selected from the group consisting of active agent for the reduction of mortality caused by sepsis.

5. The composition according to claim 3, wherein the excipients are selected from the group consisting of preservatives, stabilizers, diluents and combinations thereof.

6. The composition according to claim 3, wherein said composition is in the form of pills, capsules, chewables, tablets, effervescent tablets, intranasal, injectable solutions, particles or sublingual solutions.

* * * * *